(12) United States Patent
Czupalla et al.

(10) Patent No.: US 10,383,507 B2
(45) Date of Patent: Aug. 20, 2019

(54) STERILE SLEEVE FOR A MEDICAL VIEWING INSTRUMENT, AND METHOD FOR OPERATING A MEDICAL VIEWING INSTRUMENT

(71) Applicant: Karl Storz SE & Co. KG, Tuttlingen (DE)

(72) Inventors: Christian Czupalla, Singen (DE); Markus Kupferschmid, Emmingen-Liptingen (DE); Benedikt Köhler, Wurmlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 228 days.

(21) Appl. No.: 14/813,667

(22) Filed: Jul. 30, 2015

(65) Prior Publication Data

US 2016/0038013 A1   Feb. 11, 2016

(30) Foreign Application Priority Data

Aug. 8, 2014  (DE) .................. 10 2014 111 354

(51) Int. Cl.
*A61B 1/00* (2006.01)
*A61B 1/04* (2006.01)
(Continued)

(52) U.S. Cl.
CPC ...... *A61B 1/00142* (2013.01); *A61B 1/00032* (2013.01); *A61B 1/04* (2013.01);
(Continued)

(58) Field of Classification Search
CPC ............ A61B 1/00131; A61B 1/00135; A61B 1/00142; A61B 1/00144; A61B 46/00;
(Continued)

(56) References Cited

U.S. PATENT DOCUMENTS

| 5,800,483 A | 9/1998 | Vought |
| 5,970,980 A | 10/1999 | Adair |
| 2005/0085692 A1* | 4/2005 | Kiehn ................ A61B 1/00105 600/130 |

(Continued)

FOREIGN PATENT DOCUMENTS

| DE | 20221380 U1 | 10/2005 |
| DE | 102011054031 A1 | 10/2012 |

(Continued)

OTHER PUBLICATIONS

German Search Report, dated Mar. 13, 2015, (12 pages).
European Search Report Application No. EP15180001.8 Completed: Dec. 4, 2015;dated Dec. 15, 2015 9 pages.

*Primary Examiner* — Ryan N Henderson
(74) *Attorney, Agent, or Firm* — Whitmyer IP Group LLC

(57) ABSTRACT

A sterile sleeve for a medical viewing instrument, in particular for an endoscope, exoscope or surgical microscope, designed to enclose at least one heat-emitting component of the medical viewing instrument, has an air inlet, an air outlet, and means for conveying and/or guiding an air stream from the air inlet through the sterile sleeve to the air outlet in order to carry off the heat emitted by the at least one heat-emitting component. The invention also relates to a method for operating a medical viewing instrument, in particular an endoscope, exoscope or surgical microscope.

14 Claims, 2 Drawing Sheets

(51) Int. Cl.
*A61B 1/06* (2006.01)
*A61B 1/12* (2006.01)
*A61B 46/00* (2016.01)
*A61B 46/10* (2016.01)

(52) U.S. Cl.
CPC ............ *A61B 1/042* (2013.01); *A61B 1/0669* (2013.01); *A61B 1/128* (2013.01); *A61B 46/00* (2016.02); *A61B 46/10* (2016.02)

(58) Field of Classification Search
CPC ........... A61B 46/10; A61B 46/13; A61B 1/04; A61B 1/042; A41D 13/002; A41D 13/0025; A41D 13/005; A41D 13/0051; A41D 13/0053; A41D 13/0058
USPC ................ 600/105, 109–113, 121–125, 133, 600/155–159, 160–181; 359/510
See application file for complete search history.

(56) References Cited

U.S. PATENT DOCUMENTS

| | | | | |
|---|---|---|---|---|
| 2006/0111610 | A1* | 5/2006 | Machida | A61B 1/00082 600/116 |
| 2008/0242927 | A1* | 10/2008 | Hirata | G02B 23/2492 600/109 |
| 2009/0259103 | A1* | 10/2009 | Hirata | A61B 1/00154 600/114 |
| 2011/0290257 | A1* | 12/2011 | Hillis | A61B 19/38 128/847 |
| 2014/0058202 | A1* | 2/2014 | Rife | H02H 7/06 600/133 |

FOREIGN PATENT DOCUMENTS

| | | |
|---|---|---|
| WO | 2011041665 A2 | 4/2011 |
| WO | 2014025702 A1 | 2/2014 |

* cited by examiner

STERILE SLEEVE FOR A MEDICAL VIEWING INSTRUMENT, AND METHOD FOR OPERATING A MEDICAL VIEWING INSTRUMENT

FIELD OF THE INVENTION

The present invention relates to a sterile sleeve for a medical viewing instrument, in particular for an endoscope, an exoscope and/or a surgical microscope, said sterile sleeve being designed for enclosing at least one heat-emitting component of the medical viewing instrument, and also to a method for operating a medical viewing instrument.

BACKGROUND OF THE INVENTION

In surgical interventions, medical viewing instruments are often used that provide an image of an operating site. In this way, for example, it is possible to obtain an enlarged view of the operating site or, in the case of endoscopic operations, a view of the inside of the body. Moreover, these viewing instruments can make the intervention less tiring and/or can improve the awareness of the operating surgeon and, if appropriate, of further personnel, and they can allow the image to be recorded, for example for documentation purposes.

It is known, for example, to use an endoscope to obtain an endoscopic image of a cavity within the body in which a surgical intervention is performed. Endoscopes typically comprise a rigid or flexible elongate shaft, which is suitable for insertion into the cavity and at the distal end area of which (i.e. the area remote from the observer) an objective lens is provided for generating an image of an object field in the cavity. At the proximal end of the endoscope (i.e. the end near the observer), there is often an electronic camera for recording the image conveyed through the shaft to the proximal end via an image carrier. Since there is generally insufficient light in the observed cavity, the required illumination light is usually generated in the proximal end area of the endoscope, or coupled into the latter, and carried through the shaft to the distal end.

Moreover, surgical microscopes are known with which it is possible to generate an enlarged image of an operating site during open surgery. A surgical microscope also often has an electronic camera and an illuminating device. DE 10 2011 054 031 A1 discloses a device for viewing and illuminating an object field on a patient from a position set apart from the patient's body, which device has, at the distal end of a shaft, a head part that is widened in relation to the shaft and that has illumination for lighting purposes and has a lens system for viewing the object field, wherein the image taken is conveyed to a proximal end of the shaft, where a video camera can be coupled. A device of this kind with which an operating site can be illuminated and viewed in a surgical intervention from a working distance of 25 to 75 cm, for example, is designated as an exoscope. Exoscopes of this type are sold under the name VITOM® by Karl Storz GmbH & Co. KG. To hold a surgical microscope or an exoscope in a suitable position with respect to the operating site, a holding arrangement can be provided which can have an articulated arm that can be adjusted and fixed according to the specific requirements.

The instruments used in a surgical operation in a sterile area must be sterile. This cannot always be completely guaranteed in the case of the aforementioned viewing instruments, particularly if they comprise an electronic camera, since they are often not suitable for all sterilization methods, for example for autoclaving. It is therefore known for viewing instruments of this kind, or for the not completely sterile parts of the viewing instruments, to be covered with a sterile sleeve. Such a sterile sleeve or "drape" prevents microorganisms passing from the not completely sterile part of the viewing instrument to the operating area. In particular, the sterile sleeve ensures that, upon contact with a not completely sterile instrument, microorganisms are not transferred to surfaces or materials coming into contact with the operating site.

It is known from DE 202 21 380 U1 that a surgical microscope system for use in a sterile working atmosphere is covered partially with a sterile drape. The space enclosed by the drape is sealed off by means of a flange on an arm of the microscope stand. A suction unit, which contains a pump, can be provided for removal of medium from the drape. After the sterile drape has been arranged around the surgical microscope and has been secured by means of the flange on the arm of the stand, the space enclosed by the drape has air removed by the pump. To permit simple and rapid exchange of the drape between two surgical interventions, the drape can be ventilated by operating the pump in a reverse state, in which air is pumped from outside into the area enclosed by the drape.

Medical viewing instruments of the type described, in particular endoscopes, exoscopes and surgical microscopes, have components that heat during the use of the viewing instrument and emit heat to their surroundings. Examples of such components are electronic cameras and, if appropriate, light sources or light attachments integrated into the viewing instrument. If such a heat-emitting component of the viewing instrument is surrounded by a sterile sleeve, the emission of heat from the component to the environment is restricted or no longer possible. This can result in an overheating of the component in question, which may lead to reduced image quality and/or may damage the component in question or reduce its useful life.

SUMMARY OF THE INVENTION

The object of the present invention is to make available a sterile sleeve for a medical viewing instrument and a method for operating a medical viewing instrument, in which method the stated disadvantages are avoided as far as possible. It is in particular the object of the present invention to make available a sterile sleeve for a medical viewing instrument and a method for operating a medical viewing instrument, wherein the heat emitted by a heat-emitting component of the viewing instrument can be carried off.

This object is achieved by a device and method as per the invention.

Advantageous developments of the invention are set forth in the dependent claims.

A sterile sleeve according to the invention is designed to at least partially enclose a medical viewing instrument, in particular an endoscope, an exoscope or a surgical microscope. Medical viewing instruments of this kind are often not able to be sterilized, or they comprise one or more parts that are not able to be sterilized or that are only able to be sterilized incompletely. The use of sterile sleeves also allows the non-sterile medical product to be used in rapid succession, since the sterilization step can be omitted. The sterile sleeve is designed to enclose the medical viewing instrument, or at least a part thereof that cannot be sterilized or that cannot be completely sterilized, in order to ensure the sterile state of a sterile area in which or near which the medical viewing instrument is used, particularly in a surgical procedure.

The sterile sleeve according to the invention is preferably flexible, in particular flexurally slack, and for this purpose is preferably made of a flexible, transparent plastic film. A sterile sleeve of this kind is designed in particular as a sterile cover, which is also referred to as a "drape". However, the sterile sleeve can also be flexible in some parts and stiff in some parts, or it can also be stiff in its entirety, wherein the stiff parts are in particular made of a transparent plastics material. The sterile sleeve can have openings, for example for the passage of cables or holding arms. Control elements of the viewing instrument, which elements are likewise enclosed by the sterile sleeve, may still be actuated, for example through the plastic film or with the aid of special control areas of the sterile sleeve. In terms of its size and shape, the sterile sleeve can be adapted to the viewing instrument that is to be enclosed, such that the view and freedom of movement of the operating surgeon are not restricted any more than is necessary.

The sterile sleeve according to the invention is designed for enclosing at least one such component of the medical viewing instrument that emits heat while it is operating. Examples of a heat-emitting component of this kind are an electronic camera or a camera unit, or also a light source or a light attachment. In particular, the sterile sleeve according to the invention is designed for enclosing an electronic camera or a camera unit. Such a camera or camera unit, which can comprise further electronic elements, is generally not able to be sterilized, in particular not able to be autoclaved. The sterile sleeve can be designed to completely or partially enclose further components of the medical viewing instrument and/or further devices, for example cables, control systems or holding arms of the viewing instrument.

According to the invention, the sterile sleeve has at least one air inlet, at least one air outlet, and means for conveying and/or guiding an air stream from the air inlet through the sterile sleeve to the air outlet. The sterile sleeve is therefore designed in particular in such a way that air delivered through the at least one air inlet can be conveyed or guided at least through a partial area of a space enclosed by an outer wall of the sterile sleeve and can leave the sterile sleeve again through the at least one air outlet. In the case of a sterile sleeve designed with one wall, the air stream can be conveyed or guided at least through a partial area of an interior formed by the sterile sleeve. In the case of a sterile sleeve with more than one wall, the air stream can be conveyed or guided through an interior formed by an inner wall of the sterile sleeve and/or through a gap formed between the inner wall and an outer wall, or at least through a partial area of the interior or of the gap. The interior is designed to receive the at least one heat-emitting component of the medical viewing instrument, which component can preferably be received in a partial area of the interior through which a stream of air can flow. Apart from the at least one air inlet and the at least one air outlet, the sterile sleeve preferably has a substantially gas-tight design.

The means provided for conveying the air stream can in particular be in the form of means that generate an air stream and that effect an active delivery of air and thus cause the air to be blown into the sterile sleeve. The means for guiding the air stream comprise in particular means for leading the air stream in a predefined direction or along a predefined path inside the interior and/or the gap in the sterile sleeve. In particular, with the means for conveying and/or guiding the air stream, it is possible to generate or permit a flow of air from the air inlet to the air outlet along a predefined path inside the sterile sleeve. The heat emitted by the at least one heat-emitting component while it is operating is carried off by the air stream to the exterior of the sterile sleeve. For this purpose, the sterile sleeve can be adapted to the respective structure and/or mode of operation of the medical viewing instrument. In particular, the means for conveying and/or guiding the air stream can be designed in such a way that a sufficiently strong air stream can be guided along a heat-emitting surface of the component or close to a heat-emitting surface of the component, in order to carry off the emitted heat in such a way that the temperature of the component remains substantially constant, or at least within an admissible temperature range, while it is operating.

By virtue of the fact that the sterile sleeve has an air inlet, an air outlet, and means for conveying and/or guiding an air stream through the sterile sleeve, it is possible for a forced convection to be generated or permitted, which improves the dissipation of the lost heat that is emitted by a heat-emitting component of the viewing instrument enclosed by the sterile sleeve. The sterile sleeve is thus designed in such a way that an air stream through the sterile sleeve can be generated or permitted in order to cool the at least one heat-emitting component of the viewing instrument enclosed by the sterile sleeve. It is thereby also possible to avoid inadmissible heating of such a heat-emitting component of the medical viewing instrument that is not sterile or not able to be sterilized and that therefore has to be enclosed by a sterile sleeve during use in or near a sterile area.

According to a preferred embodiment of the invention, the means for conveying and/or guiding the air stream comprise at least one ventilator and/or at least one pump, the term "ventilator" generally standing for continuous-flow machines and the term "pump" generally standing for displacement machines that drive the air stream and thus in particular are able to effect an active delivery of air, i.e. allow air to be blown into the sterile sleeve. The ventilator or the pump is preferably integrated in the sterile sleeve. By virtue of the fact that the sterile sleeve comprises a ventilator or a pump for conveying and/or guiding the air stream, it is easy to generate a forced convection in order to carry off heat. Moreover, the use of the sterile sleeve is made easier, and it is easier to operate the sterile sleeve together with the medical viewing instrument enclosed by it.

In addition or alternatively, the sterile sleeve can have an attachment for an external active air delivery, wherein air is delivered from an external air delivery unit, for example via an attachable air hose. An external air delivery unit of this kind can be assigned, for example, to an external light source, which generally has a ventilator for cooling the light source, which ventilator, according to this aspect of the invention, can be used to generate an air stream guided through the sterile sleeve in order to cool the heat-emitting component of the medical viewing instrument. In this way too, it is easy to achieve an active delivery of air for generating a forced convection for carrying off heat.

Preferably, the sterile sleeve further comprises an electrical energy source for powering the ventilator or the pump enclosed by the sterile sleeve. The electrical energy source can in particular be a battery or an accumulator. In this way, an autonomous power supply is permitted in particular for an active delivery of air to the sterile sleeve, as a result of which the use of the sterile sleeve and the start-up thereof for cooling the at least one heat-emitting component are further facilitated. Alternatively, the ventilator or the pump can be powerable from an external energy source.

Preferably, the ventilator or the pump and/or the energy source for powering the ventilator or the pump is/are connected releasably, and thus exchangeably, to the sterile sleeve. The ventilator or the pump can be inserted, particularly in a sealed-off manner, into an opening provided for this purpose in the sterile sleeve and it can be removed again from the opening. This permits re-use of the ventilator or the pump and/or of the electrical energy source, while the rest of the sterile sleeve can be designed as a disposable part to be discarded after one use. Alternatively, the ventilator or the pump and/or the electrical energy source can likewise be designed as a disposable part.

According to a preferred embodiment of the invention, the sterile sleeve comprises a plurality of air-guiding chambers communicating with one another and with the air inlet and the air outlet in terms of flow, which chambers are designed to guide at least part of the air stream. In particular, an interior enclosed by the sterile sleeve and/or a gap formed between an inner wall and an outer wall of the sterile sleeve is/are divided into a plurality of air-guiding chambers of this kind. This allows at least part of the air stream to be guided along a predetermined path through the sterile sleeve. In particular, the plurality of air-guiding chambers can be designed to provide a separation of the inflowing air and outflowing air, such that air flowing in through the air inlet is guided to a heat-emitting surface of the heat-emitting component, takes up heat there and is thereafter guided to the air outlet, without mixing with the inflowing air. It is thus possible for the heat loss from the heat-emitting component of the medical viewing instrument to be carried off in a particularly efficient way.

Preferably, the sterile sleeve is designed at least in some parts with more than one wall, in particular with a double wall, wherein at least one air-guiding chamber is arranged between an inner wall and an outer wall for the purpose of guiding at least part of the air stream through the gap formed between the inner wall and the outer wall. The air-guiding chamber can be delimited by the inner wall and the outer wall and/or one or more intermediate walls arranged between the inner wall and the outer wall. An air-guiding chamber of this kind can be designed in particular as an air channel through which at least part of the air stream is guided from the at least one air inlet to the at least one air outlet. In addition, a part of the air stream can be guided through the interior enclosed by the inner wall of the sterile sleeve. Alternatively, the interior can be closed off in a substantially gas-tight manner, such that a heat transfer from the heat-emitting component to the inner wall of the sterile sleeve takes place by thermal convection and, from there, the heat is carried off by the air stream and thus by forced convection. By virtue of the fact that at least one air-guiding chamber is provided between the inner wall and the outer wall for the purpose of guiding at least a part of the air stream through the gap between the inner wall and the outer wall, heat is able to be carried off in a particularly efficient way. If an area of the interior which is enclosed by the inner wall, and in which the at least one heat-generating component can be arranged, has a substantially gas-tight configuration, particularly high sterility requirements can be satisfied, or lower requirements can be set concerning the sterility of the component of the viewing instrument received therein. If, on the other hand, part of the air stream is guided through the area of the interior in question, it is possible to achieve a further improvement in the way the heat is carried off.

Furthermore, it is preferable that the air stream in the at least one air-guiding chamber is guided in a turbulent fashion. For this purpose, obstacles, projections, constrictions, curvatures and/or roughened surfaces can be provided inside the air-guiding chamber or inside an air channel, for example, as a result of which the turbulence of the air flow is increased. The turbulent air flow permits a particularly efficient uptake of heat by the air stream and, consequently, the heat loss generated by the heat-emitting component is carried off in a particularly efficient way.

Preferably, the sterile sleeve is designed in such a way that an overpressure can be generated in the sterile sleeve, for example by an active delivery of air by means of a ventilator or a pump. Preferably, if the sterile sleeve is flexible or flexurally slack at least in some parts, the overpressure generated inside the at least one air-guiding chamber, or in the interior, can permit a stabilization of the shape of the sterile sleeve, which stabilization facilitates the handling of the sterile sleeve with the viewing instrument at least partially enclosed by the latter. In particular, an overpressure sufficient for this purpose can be generated in the interior enclosed by an inner wall of the sterile sleeve or in at least one air-guiding chamber in the interior and/or in the gap between the inner wall and an outer wall. Thus, for example, a cross section of flow of the at least one air-guiding chamber and/or of the at least one air outlet can be designed in such a way that, in the case of an active delivery of air, a suitable overpressure arises in the at least one air-guiding chamber or in the interior on account of the flow resistance. In this case, the sterile sleeve is in particular designed in such a way that, when the at least one air-guiding chamber is "inflated" by the overpressure, the sterile sleeve adopts a desired shape that facilitates handling and that does not obstruct the view and the freedom of movement of the operating surgeon. Moreover, the sterile sleeve is advantageously designed in such a way that, when an overpressure sufficient for the shape stabilization is generated, an air stream with a sufficient heat dissipation effect is generated at the same time. The usability of the sterile sleeve is further facilitated by this.

According to a preferred embodiment of the invention, the sterile sleeve is designed at least in some parts to be flexible and have more than one wall, at least a double wall comprising an inner wall and an outer wall, wherein at least one support chamber is arranged between the inner wall and the outer wall, within which support chamber an overpressure can be generated by an active delivery of air. The support chamber can be delimited by the inner wall and the outer wall and/or one or more intermediate walls arranged between the inner wall and the outer wall. The at least one support chamber does not have an air stream passing through it, but it is designed in such a way that the chamber is "inflated" by the overpressure and thus stabilized in a shape that confers a desired shape on the previously flexurally slack sterile sleeve as a whole. Therefore, in the state when subjected to an overpressure, the at least one support chamber represents a support structure which in particular stabilizes the sterile sleeve. Particularly preferably, a plurality of support chambers are provided which form a column structure or honeycomb structure, thus permitting a particularly effective stabilization of the sterile sleeve. The shape stabilized in this way is in particular adapted to the shape and the size of the medical viewing instrument enclosed at least partially by the sterile sleeve. The shape is preferably determined in such a way that a particularly effective flow of air through the at least one air-guiding chamber is ensured, wherein the stabilized shape is able to enforce, if appropriate, a turbulent flow of the air in the at least one air-guiding chamber. In this way, a further improvement in the heat dissipation effect and improved handling of the sterile sleeve can easily be achieved, and, in the state when not in use, the sterile sleeve is able to adopt any desired shape, so as to make storage easier.

According to another preferred embodiment, the sterile sleeve has a self-stabilizing support structure, which is formed, for example, by rods or wires incorporated into the sterile sleeve. In this way too, it is possible to achieve a stabilization of the sterile sleeve and an improvement in the flow of air in the at least one air-guiding chamber, wherein the sterile sleeve is adapted in particular to the shape and size of the viewing instrument enclosed at least partially by the sterile sleeve.

Alternatively or in addition, the sterile sleeve can be stiff in some parts or stiff all over, in particular inherently stiff and therefore self-stabilizing, and for this purpose can be made, at least in some parts, from a solid and preferably transparent plastics material. The plastics material preferably has a sufficiently thick wall to ensure that the sterile sleeve can be gripped and handled without appreciable deformation. The sterile sleeve can be composed of at least two parts, for example two halves, which halves can be separated from each other, such that the component of the medical viewing instrument to be enclosed can be received and can be removed, and which halves can be connected to each other in a substantially airtight manner, for example by being plugged together, so as to enclose the component. If the enclosed component of the viewing instrument has control elements, these can be actuated with the aid of corresponding control areas of the sterile sleeve, wherein the control areas can, for example, be flexible areas of a sterile sleeve that is stiff in some parts. A sterile sleeve that is stiff in at least some parts can be advantageous for the maneuverability of the viewing instrument in or near a sterile area.

Preferably, the air outlet is provided with a filter and/or a valve. The filter is preferably designed in such a way that it is impermeable to dirt particles and microorganisms, which could detach themselves from a surface of a non-sterile instrument enclosed by the sterile sleeve. Moreover, the air outlet is in particular arranged in such a way that the air flowing out is remote from the area of the object field, in particular an operating site, viewable with the endoscopic viewing instrument, i.e. the air flows out of the air outlet in the direction away from said site, and/or the air outlet is arranged at an end of the sterile sleeve that is directed away from or remote from the object field or from the operating site while the viewing instrument is being operated. In this way, the entry of dirt or of microorganisms into the area of the operating site can be avoided still more reliably.

Moreover, the filter or the valve is preferably designed in such a way that, in the case of an active delivery of air, an overpressure can be generated within the at least one air-guiding chamber and/or the at least one support chamber, in order to achieve a support action, as has been described above for an at least partially flexible sterile sleeve, and to stabilize the sterile sleeve in a desired shape. For this purpose, the valve can also be designed to be adjustable, for example.

According to another preferred embodiment, the sterile sleeve is made at least partially of an air-permeable material. In particular, an outer wall of the sterile sleeve is made, at least in some parts, of the air-permeable material, which forms at least one air outlet. A material of this kind can be, for example, a film with a microporosity that allows air to flow out but prevents the passage of dirt and/or microorganisms. It is thus possible to guide the air stream through the sterile sleeve in a particularly simple way and, in particular, to design an air outlet from the sterile sleeve in a two-dimensional form and arrange it in any desired areas of the sterile sleeve. In this way, overheating of individual areas of the sterile sleeve can be particularly safely prevented. Contamination of the operating site can be substantially avoided since, even in the case of a non-sterile viewing instrument enclosed by the sterile sleeve, microorganisms pass into the air stream only in small measure and they are additionally held back on passage through the porous material of the sterile sleeve. Therefore, despite the air permeability of the material, contamination of the viewing instrument can likewise be avoided during the operation.

According to a preferred embodiment of the invention, the sterile sleeve comprises a cover glass that can be fixed on a distal window of the viewing instrument enclosed by the sterile sleeve. The distal window is inserted in a gas-tight manner into the sterile sleeve. This, on the one hand, permits an unimpeded view using the viewing instrument and, on the other hand, fixes the sterile sleeve on the viewing instrument. Moreover, contamination of the viewing instrument can be avoided during an operation.

According to an alternative preferred embodiment of the invention, the sterile sleeve has an opening which can be attached in a gas-tight manner to a distal window of the viewing instrument. For this purpose, the opening can be surrounded in particular by a seal, which is adapted for attachment to the distal window of the viewing instrument, which window can be closed off by a cover glass assigned to the viewing instrument. This too, on the one hand, permits an unimpeded view of the operating site with the viewing instrument and, on the other hand, secures the sterile sleeve on the medical viewing instrument at least partially enclosed by it.

As an alternative securing possibility, one or more adhesive surfaces can be arranged on an inner face of the sterile sleeve. This too can easily allow the sterile sleeve to be fixed on the medical viewing instrument enclosed by it, so as to facilitate the handling of the viewing instrument.

In a method according to the invention for operating a medical viewing instrument, in particular an endoscope, exoscope or surgical microscope, the medical viewing instrument, or at least a heat-emitting component of the viewing instrument, is enclosed by a sterile sleeve which is designed as described above. If appropriate, the sterile sleeve may have been prepared in advance by insertion of a ventilator or of a pump together with an electrical energy source. Moreover, the medical viewing instrument now at least partially received in the sterile sleeve is arranged to view an operating site. For example, an exoscope or a surgical microscope is secured on a holding arm, which can likewise be partially enclosed by the sterile sleeve, and is held at a suitable distance above the operating site. In the case of an endoscope, a video camera, for example, which has been enclosed with the sterile sleeve, can be attached to the endoscope. The heat-emitting component, for example a video camera, is then started up, whereupon heat loss is released. To carry off the heat loss, an active delivery of air to the sterile sleeve is started up, for example a ventilator or a pump integrated in the sterile sleeve, or an external air delivery device is attached to the air inlet of the sterile sleeve via an air hose and started up. In this way, an air stream is conveyed from the air inlet through the sterile sleeve, in particular through the interior enclosed by an inner wall of the sterile sleeve and/or through a gap formed between the inner wall and an outer wall of the sterile sleeve, wherein the air stream is guided, preferably by air-guiding chambers, along a heat-emitting surface of the heat-emitting component or is guided around the component. In this way, the heat loss released during the operation of the heat-emitting component can be carried off in an improved manner, and overheating of the heat-emitting component can be avoided while it is operating.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

Further aspects of the invention will become clear from the following description of a preferred illustrative embodiment and from the attached drawing, in which.

DETAILED DESCRIPTION OF THE INVENTION

Figure 1:
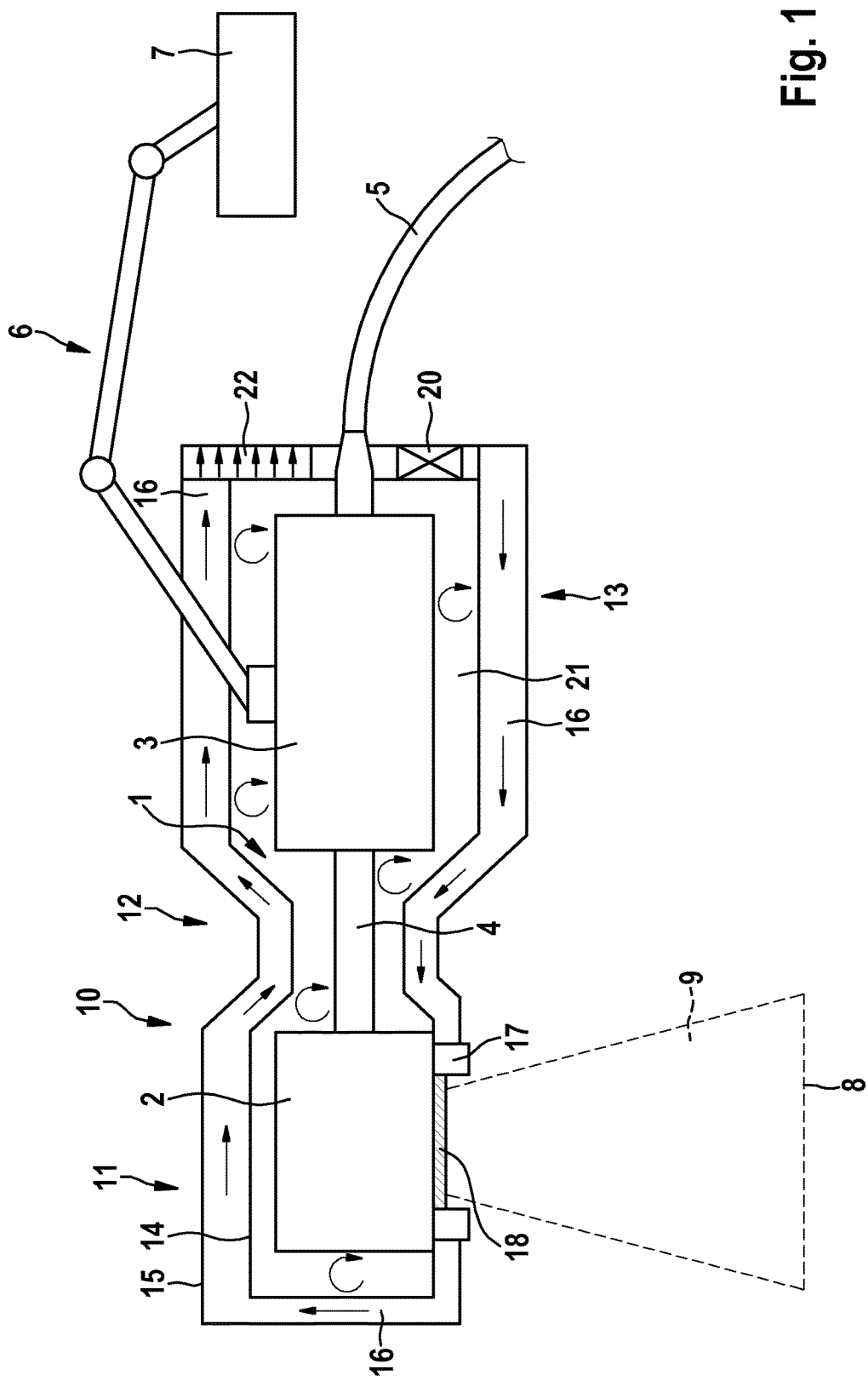
FIG. 1 shows a schematic sectional view of a first illustrative embodiment of a sterile sleeve according to the invention, with an exoscope enclosed by said sterile sleeve.

As is shown in FIG. 1 in a schematic longitudinal section, an exoscope 1 in use in an operating theater is enclosed by a sterile sleeve 10. The sterile sleeve 10 can be flexible, in particular flexurally slack, or it can be stiff, in particular inherently stiff. The exoscope 1 comprises a head 2 in which an illuminating device, for illuminating an object field 8, for example an operating site, is arranged along with an objective lens. The exoscope 1 moreover comprises a camera unit 3 which is connected to the head 2 of the exoscope 1 via a shaft 4. The shaft 4 accommodates electrical lines, for powering the illuminating device arranged in the head 2, and also an image carrier which, for example, can be formed by an ordered bundle of fibers or by relay lens systems, for forwarding the image of the object field 8 taken by the objective lens. The camera unit 3 is connected by a power cable 5 to a device (not shown) for power supply and evaluation. By means of a holding arm 6, which is designed as an articulated arm and sits on a fixed structure 7 of the operating theater, the exoscope 1 is held in a position suitable for viewing the object field 8.

Since the exoscope 1 can be sterilized only to a limited extent, it is enclosed by a sterile sleeve 10. The latter has a distal portion 11, which is designed to enclose the head 2 of the exoscope 1, a shaft portion 12, which encloses the shaft 4, and a proximal portion 13, of which the shape and size are adapted to enclose the camera unit 3 of the exoscope 1. The sterile sleeve 10 has two walls, wherein chambers through which air can flow or which can be filled with air are arranged between the inner wall 14 and the outer wall 15. A chamber through which air can flow, and which is designed as an air channel 16, is shown in FIG. 1 between the inner wall 14 and the outer wall 15. The air channel 16 is divided by intermediate walls (not shown in FIG. 1) from further air-guiding channels and, if appropriate, from support chambers, which can likewise be arranged between the inner wall 14 and the outer wall 15.

The distal portion 11 of the sterile sleeve 10 has a cover glass 18, which is inserted in a gas-tight manner into a plastic insert 17, which is in turn connected in a gas-tight manner to the inner wall 14 and the outer wall 15. The plastic insert 17 and the cover glass 18 are dimensioned and arranged in such a way that the illuminating device and the objective lens accommodated in the head 2 of the exoscope 1 can act through the cover glass 18, as is indicated symbolically in FIG. 1 by the cone of light 9. The air channel 16 is routed around the cover glass 18 and around the plastic insert 17.

The proximal portion 13 of the sterile sleeve 10 has an opening (not shown in FIG. 1) for passage of the holding arm 6, and an opening (likewise not shown) for passage of the power cable 5. Sealing means not shown in FIG. 1, for example rubber bands, are provided at both openings, such that the sterile sleeve 10 is closed off in a gas-tight manner on the holding arm 6 and on the power cable 5. In its proximal portion 13, the sterile sleeve 10 further comprises a ventilator 20, which can be operated to deliver air into the air channel 16 and, if appropriate, into the interior 21 which is surrounded by the inner wall 14 of the sterile sleeve 10 and in which the exoscope 1 is received. If the sterile sleeve 10 is flexible, the ventilator 20 can be designed to deliver air into the support chambers (not shown in FIG. 1), which are arranged between the inner wall 14 and the outer wall 15, and to generate an overpressure in these chambers, such that the sterile sleeve 10 is thereby stabilized in a shape enclosing the exoscope 1 at a distance. If the sterile sleeve 10 is inherently stiff, it likewise encloses the exoscope 1 at a distance, wherein the exoscope 1 is held in the sterile sleeve 10 and can be handled with the aid of the grippable sterile sleeve 10. The ventilator 20 comprises an integrated battery, which supplies it with electrical energy, and is fitted releasably, but in a sealed manner, in a corresponding opening of the sterile sleeve 10.

Furthermore, in its proximal portion 13, the sterile sleeve 10 comprises an outlet opening, in which a filter 22 is arranged through which the air delivered into the air channel 16 and, if appropriate, into the interior 21 can escape to the exterior. Particularly in the case where air leaves the interior 21 through the outlet opening or the filter 22, the latter is designed in such a way that dirt particles and microorganisms, which could detach themselves from the not completely sterilized exoscope 1, are held back. As is indicated in FIG. 1, the outlet opening with the filter 22 is arranged at the proximal end of the proximal portion 13 of the sterile sleeve 10, i.e. at the end remote from the head 2 of the exoscope 1, such that the air leaving to the exterior is guided away from the object field 8.

To prepare for the use of the exoscope 1, the latter is covered with the sterile sleeve 10 or fitted into it. For this purpose, the sterile sleeve 10 has an opening which, for example, can be the opening through which the holding arm 6 is guided and which is dimensioned such that the exoscope 1 can be inserted into the interior 21 of the sterile sleeve 10. In this state, the ventilator 20 is not yet operating, such that the interior 21 or the air channel 16 or, if appropriate, the support chambers divided off between the inner wall 14 and the outer wall 15 of the sterile sleeve 10 are not subjected to an overpressure. If the sterile sleeve 10 is made substantially of a flexible, transparent plastic film, it is therefore flexurally slack and easy to handle. If the sterile sleeve 10 is stiff and for this purpose is made of a solid plastics material, it can be composed of two halves which, after the exoscope 1 has been inserted, can be connected to each other in an airtight manner (not shown in FIG. 1). The cover glass 18 integrated in the sterile sleeve 10 is arranged in front of the illumination optics and the objective lens of the exoscope 1 and fixes the plastic insert on the head 2 of the exoscope 1, for which reason the plastic insert 17 and the head 2 can have locking elements interacting with one another. When the exoscope 1 has been inserted into the interior 21 of the sterile sleeve 10, the connecting cable 5 is attached to the exoscope 1 and the openings of the sterile sleeve 10, through which the connecting cable 5 and the holding arm 6 are guided, are sealed off in a substantially gas-tight manner. If the ventilator 20 and the filter 22 are not rigidly integrated in the sterile sleeve 10, they are inserted into the latter before startup.

When the exoscope 1 is started up, such that heat is released in the area of the head 2 and of the camera unit 3, the ventilator 20 is also started up. The ventilator 20 conveys air into the air channel 16 and, if appropriate, into the interior 21 enclosed by the inner wall 14. If the sterile sleeve is flexible, the ventilator 20 can also convey air into the support chambers formed between the inner wall 14 and the outer wall 15; the overpressure generated in the support chambers stabilizes the sterile sleeve 10 in the predefined shape, which is optimized for enclosing the exoscope 1 and for allowing a stream of air into the air channels 16 and, if appropriate, within the interior 21, and also for handling during the surgical procedure. The air blown into the air channel 16 flows inside the air channel 16, in the direction of the arrows, through the proximal portion 13, the shaft portion 12, the distal portion 11, through the shaft portion 12 again, and back to the proximal portion 13 of the sterile sleeve 10, where it reaches the outlet opening in which the filter 22 is arranged. The heat loss emitted from the exoscope 1 heats the air located in the interior 21 of the sterile sleeve 10. As is indicated in FIG. 1 by the curved arrows, the heat in the interior 21 is transported by thermal convection to the inner wall 14 of the sterile sleeve 10, where it is entrained by the air that is conveyed from the ventilator 20 and that flows in the air channel 16. If the ventilator 20 also blows air into the interior 21, at least some of the heat from this is taken up. After the heat emitted by the exoscope 1 has been taken up, the air delivered from the ventilator 20 passes through the filter 22 out of the air channel 16 and/or out of the interior 21 to the exterior and thus carries off the heat.

After completion of the operation, the exoscope 1 and, if appropriate, the ventilator 20 are removed from the sterile sleeve 10 for renewed use, and the sterile sleeve 10 and the filter 22 are disposed of.

Figure 2:
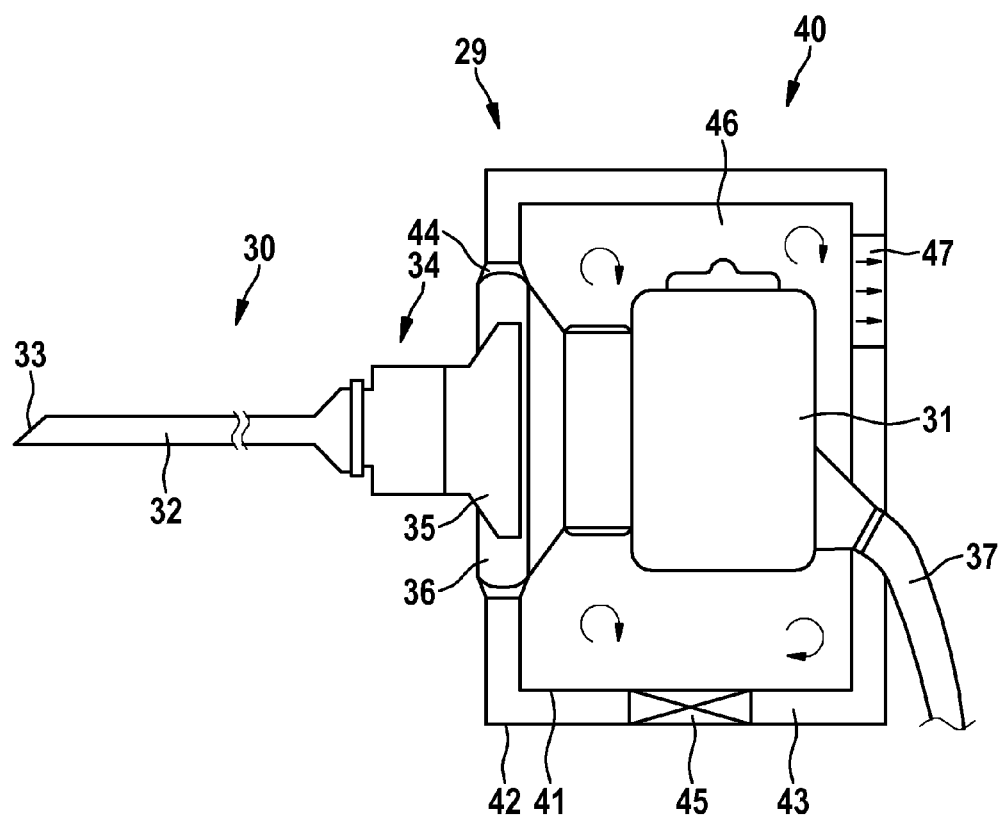
FIG. 2 shows a schematic sectional view of a second illustrative embodiment of a sterile sleeve according to the invention, with a video camera of an endoscope enclosed by said sterile sleeve.

FIG. 2 shows an endoscope 29, which comprises an endoscope lens system 30 to which a camera head 31 is attached. The endoscope lens system 30 comprises an elongate shaft 32, at the distal end 33 of which an endoscope objective lens is arranged. The endoscopic image generated by the endoscope objective lens is carried through an image carrier arranged in the shaft 32, for example an ordered bundle of fibers or one or more relay lens systems, to an eyepiece arranged in the proximal end area 34 of the endoscope lens system 30. The endoscopic image that has been generated by the endoscope objective lens and transmitted by the image carrier can be observed with the aid of the eyepiece cup 35. To operate the endoscope lens system 30 as a video endoscope, the camera head 31 is attached to the eyepiece cup 35 via an adapter 36, said camera head 31 containing an electronic camera for recording the endoscopic image. A connecting cable 37 provides the connection to a device (not shown) for power supply and evaluation.

Since the camera head 31 cannot be adequately sterilized, it is enclosed by a sterile sleeve 40 during use in an endoscopy procedure. The sterile sleeve 40 is designed with an inner wall 41 and an outer wall 42, between which a support chamber 43 is formed if the sterile sleeve 40 is flexible. The sterile sleeve 40 is attached to the adapter 36 in a gas-tight manner with a seal 44, which encloses a corresponding opening. The power cable 37 is routed in a gas-tight manner through a further opening of the sterile sleeve 40. A ventilator 45 is designed to deliver an air stream into the interior 46 of the sterile sleeve 40 and, if appropriate, to generate an overpressure in the support chamber 43. The air blown into the interior 46 leaves the latter again through an outlet opening, in which a filter 47 is fitted.

To prepare for the use of the camera head 31 with the endoscope lens system 30 in an endoscopy procedure, the camera head 31 is covered with an initially still flexurally slack sterile sleeve 40 or is inserted into two halves of a stiff sterile sleeve 40, which halves can be plugged together in an airtight manner. The sterile sleeve 40 is then attached to the adapter 36 in a gas-tight manner via the seal 44, the connecting cable 37 is attached to the camera head 31, and the opening for the connecting cable 37, which opening had served for insertion of the camera head 31 into the sterile sleeve 40, is closed off in a gas-tight manner on the connecting cable 37. If appropriate, the ventilator 45 and the filter 47 are inserted into the sterile sleeve 40. Before this or afterward, the camera head 31 is placed with the adapter 36 onto the eyepiece cup 35 of the endoscope lens system 30.

When the camera head 31 is started up, it generates heat that has to be carried off in order to avoid overheating. For this purpose, the ventilator 45 is started up. The ventilator 45 conveys air into the interior 46 of the sterile sleeve 40 enclosed by the inner wall 41 and, if appropriate, into support chambers 43 formed between the inner wall 41 and the outer wall 42. If the sterile sleeve 40 is flexible, the overpressure generated in the support chamber 43 stabilizes the sterile sleeve 40 in a predefined shape, which is optimized for enclosing the camera head 31 and for allowing a stream of air into the interior 46, and also for handling the endoscope 29. The air blown into the interior 46 takes up the heat emitted by the camera head 31, flows to the outlet opening in which the filter 47 is arranged, and passes through the latter out of the sterile sleeve 40. As is indicated by the curved arrows, the air flows in a turbulent fashion, such that a more intensive transfer of heat is ensured at the heat-emitting surfaces of the camera head 31. In this way, the heat emitted by the camera head 31 is transported to the exterior.

After completion of the operation, the camera head 31 is separated from the endoscope lens system, the camera head 31 and, if appropriate, the ventilator 45 are removed from the sterile sleeve 40, and the sterile sleeve 40 and the filter 47 are disposed of.

The invention claimed is:

1. A sterile sleeve configured to enclose a heat-emitting component of a medical viewing instrument, the sterile sleeve comprising:
an inner wall forming an interior of the sterile sleeve in which the heat-emitting component is enclosed;
an outer wall defining an exterior of the sterile sleeve;
a support chamber formed in a gap between the inner wall and outer wall; an air inlet;
an air outlet having a filter; and
an air source configured to deliver an air stream from the air inlet through the interior of the sterile sleeve to the air outlet in order to carry off heat emitted by the heat-emitting component, and configured to deliver a portion of the air stream into the support chamber, wherein the portion of the air stream delivered into the support chamber inflates the sterile sleeve into a predefined shape.

2. The sterile sleeve according to claim 1, wherein the air source comprises at least one ventilator and/or at least one pump.

3. The sterile sleeve according to claim 2, wherein the sterile sleeve comprises an electrical energy source for powering a drive of the at least one ventilator or at least one pump.

4. The sterile sleeve according to claim 2, wherein the at least one ventilator, the at least one pump, and/or an electrical energy source is/are connected releasably to the sterile sleeve.

5. The sterile sleeve according to claim 1, wherein the air-guiding chamber is a first air-guiding chamber; and
wherein the sterile sleeve has a second air-guiding chamber communicating with the first air guiding chamber and with the air inlet and the air outlet.

6. The sterile sleeve according to claim 1, wherein the air stream in the air-guiding chamber is guided in a turbulent fashion.

7. The sterile sleeve according to claim 1, wherein at least a portion of the sterile sleeve is flexible, and an overpressure suitable for inflating the sterile sleeve into a predefined shape is generated in the air-guiding chamber of the sterile sleeve.

8. The sterile sleeve according to claim 1, wherein the sterile sleeve has a self-stabilizing support structure and/or at least a portion of the sterile sleeve is stiff.

9. The sterile sleeve according to claim 1, wherein the air outlet has a valve.

10. The sterile sleeve according to claim 1, wherein the air outlet is arranged remote from and/or facing away from an object field viewable with the medical viewing instrument.

11. The sterile sleeve according to claim 1, wherein the sterile sleeve is made at least partially of an air-permeable material.

12. The sterile sleeve according to claim 1, wherein the sterile sleeve has a cover glass that can be fixed on a distal window of the viewing instrument.

13. The sterile sleeve according to claim 1, wherein the inner wall and the outer wall collectively form a double wall.

14. A system, comprising:
a heat-emitting component of a medical viewing instrument; and
a sterile sleeve configured to enclose the heat-emitting component, the sterile sleeve including:
an inner wall forming an interior in which the heat-emitting component is enclosed;
an outer wall defining an exterior of the sterile sleeve;
a support chamber formed in a gap between the inner wall and outer wall;
an air inlet;
an air outlet having a filter; and
an air source configured to deliver an air stream from the air inlet through the interior of the sterile sleeve to the air outlet in order to carry off heat emitted by the heat-emitting component, and configured to deliver a portion of the air stream into the support chamber, wherein the portion of the air stream delivered into the support chamber inflates the sterile sleeve into a predefined shape.

* * * * *